US012427323B2

United States Patent
Loo et al.

(10) Patent No.: US 12,427,323 B2
(45) Date of Patent: Sep. 30, 2025

(54) ENCAPSULATION OF EXTERNAL COMPONENTS IN ACTIVE IMPLANTABLE MEDICAL DEVICES

(71) Applicants: Verily Life Sciences LLC, South San Francisco, CA (US); David K. Peterson, South San Francisco, CA (US)

(72) Inventors: Alexander Loo, Redwood City, CA (US); Peng Cong, Burlingame, CA (US); David K. Peterson, Novato, CA (US)

(73) Assignee: Verily Life Sciences LLC, Dallas, TX (US)

( * ) Notice: Subject to any disclaimer, the term of this patent is extended or adjusted under 35 U.S.C. 154(b) by 737 days.

(21) Appl. No.: 17/597,527

(22) PCT Filed: Jul. 13, 2020

(86) PCT No.: PCT/US2020/041758
§ 371 (c)(1),
(2) Date: Jan. 10, 2022

(87) PCT Pub. No.: WO2021/007571
PCT Pub. Date: Jan. 14, 2021

(65) Prior Publication Data
US 2022/0249852 A1    Aug. 11, 2022

Related U.S. Application Data

(60) Provisional application No. 62/872,767, filed on Jul. 11, 2019.

(51) Int. Cl.
*A61N 1/37*     (2006.01)
*A61N 1/372*    (2006.01)
*A61N 1/378*    (2006.01)

(52) U.S. Cl.
CPC ....... *A61N 1/37229* (2013.01); *A61N 1/3787* (2013.01)

(58) Field of Classification Search
CPC .......................... A61N 1/3787; A61N 1/37229
See application file for complete search history.

(56) References Cited

U.S. PATENT DOCUMENTS 5,861,019 A * 1/1999 Sun ........................ H01Q 1/273
607/36
6,115,634 A    9/2000 Donders et al.
(Continued)

FOREIGN PATENT DOCUMENTS

CN    102614587 A    8/2012
CN    108541219 A    9/2018
(Continued)

OTHER PUBLICATIONS

EP Appl. 20836326.7, Extended European Search Report, Aug. 4, 2023, 9 pages.
(Continued)

*Primary Examiner* — Eric D. Bertram
(74) *Attorney, Agent, or Firm* — Kilpatrick Townsend & Stockton LLP

(57) ABSTRACT

An implantable medical device is described. The implantable medical device includes an enclosure for receiving and hermitically sealing active components. A header is connected to the enclosure and encloses other components of the device. A communications antenna is encapsulated in a bio-compatible material and connected to an exterior surface of the enclosure. The communications antenna is electrically connected to the active components via an access window of the header. The access window is backfilled after the connections are made.

21 Claims, 6 Drawing Sheets

(56) References Cited

U.S. PATENT DOCUMENTS

| | | | |
|---|---|---|---|
| 6,456,256 B1* | 9/2002 | Amundson | A61N 1/37229 343/741 |
| 7,016,733 B2* | 3/2006 | Dublin | A61N 1/37229 607/36 |
| 7,317,946 B2* | 1/2008 | Twetan | A61N 1/37229 607/57 |
| 9,955,289 B1 | 4/2018 | Liu et al. | |
| 10,779,767 B2* | 9/2020 | Li | A61B 5/29 |
| 2004/0215280 A1* | 10/2004 | Dublin | A61N 1/37229 607/36 |
| 2005/0134520 A1 | 6/2005 | Rawat et al. | |
| 2005/0203583 A1 | 9/2005 | Twetan et al. | |
| 2005/0203584 A1* | 9/2005 | Twetan | A61N 1/37229 607/36 |
| 2009/0228074 A1* | 9/2009 | Edgell | H01Q 1/40 607/60 |
| 2010/0016925 A1 | 1/2010 | Christman et al. | |
| 2010/0082080 A1* | 4/2010 | Mateychuk | A61N 1/37229 607/60 |
| 2010/0100157 A1 | 4/2010 | Nghiem et al. | |
| 2010/0161002 A1 | 6/2010 | Aghassian et al. | |
| 2011/0001610 A1 | 1/2011 | Stevenson et al. | |
| 2011/0137414 A1 | 6/2011 | Litzke et al. | |
| 2014/0214130 A1 | 7/2014 | Lopez et al. | |
| 2014/0266921 A1 | 9/2014 | Joshi | |
| 2014/0364714 A1* | 12/2014 | Ameri | A61N 1/375 607/60 |
| 2015/0257755 A1 | 9/2015 | North | |
| 2016/0023012 A1 | 1/2016 | Ries et al. | |
| 2016/0285158 A1 | 9/2016 | Meulmester et al. | |
| 2016/0359222 A1 | 12/2016 | Li et al. | |
| 2017/0281957 A1* | 10/2017 | Howard | A61N 1/37229 |
| 2018/0042552 A1 | 2/2018 | Li et al. | |
| 2018/0069303 A1 | 3/2018 | Li et al. | |
| 2018/0185661 A1 | 7/2018 | Imran et al. | |
| 2019/0060656 A1 | 2/2019 | Scott et al. | |
| 2020/0094064 A1 | 3/2020 | Cong | |

FOREIGN PATENT DOCUMENTS

| | | |
|---|---|---|
| WO | 2006126201 | 11/2006 |
| WO | 2020068652 A1 | 4/2020 |

OTHER PUBLICATIONS

International Application No. PCT/US2019/052403, International Search Report and Written Opinion, Mailed On Nov. 19, 2019, 16 pages.
International Application No. PCT/US2020/041758, International Search Report and Written Opinion, Mailed On Oct. 7, 2020, 16 pages.
CN202080061980.X, Office Action, May 30, 2025.
China Appl. No. 202080061980.X, Notice of Decision to Grant, Aug. 25, 2025.

* cited by examiner

ENCAPSULATION OF EXTERNAL COMPONENTS IN ACTIVE IMPLANTABLE MEDICAL DEVICES

BACKGROUND

Implantable medical devices typically include electronics, batteries, antennae, and other active and passive components. These components are hermetically sealed within an enclosure or otherwise encapsulated to prevent moisture ingress. For example, a communications antenna may be attached to the enclosure and the header may be formed in-place by over-molding (e.g., using a biocompatible epoxy to encapsulate the components).

BRIEF SUMMARY

Various examples are described relating to implantable medical devices, implantable systems, and methods for forming implantable medical devices.

One general aspect includes an implantable device, including: an enclosure including a lid and a side wall connected to the lid. The implantable device also includes an electronics assembly disposed within an interior volume of the enclosure. The implantable device also includes a set of conductive leads electrically connected to the electronics assembly and extending through the enclosure. The implantable device also includes a communications antenna disposed on an exterior surface of the side wall and including a main body and a tab, the tab including a set of conductive terminals, where the main body is coated in a bio-compatible material and the set of conductive terminals is electrically connected to the set of conductive leads.

Another general aspect includes a method, including: providing an enclosure including an electronics assembly. The method also includes coupling a header to enclose at least a lid of the enclosure, where an access window is formed at a perimeter edge of the header and a set of conductive leads extend from the electronics assembly and through the access window. The method also includes connecting a communications antenna to an exterior surface of a side wall of the enclosure. The communications antenna including a body and an electrical termination tab that corresponds in size and shape to the access window and aligns a set of conductive terminals disposed in the electrical termination tab with the set of conductive leads.

Another general aspect includes a system, including: an implantable medical device and an antenna. The implantable medical device also includes an enclosure to house an electronics assembly, the enclosure including a lid and a side connected to the lid. The implantable medical device also includes a set of conductive leads to extend from the electronics assembly to outside the enclosure via the lid. The antenna connects to an exterior surface of the side at a mounting location. The antenna includes a body portion encased in a bio-compatible material, a tab portion connected to the body portion, and a set of conductive terminals disposed in the tab portion and that align with the set of conductive leads when the antenna is connected to the exterior surface at the mounting location.

Another general aspect includes a device, including: an enclosure including a lid and a side wall. The device also includes an electronics assembly disposed within an interior volume of the enclosure and including a plurality of conductive leads that extend through the lid of the enclosure. The device also includes one or more electrical components connected to an exterior surface of the lid and electrically connected to a first portion of the plurality of conductive leads. The device also includes a header that encapsulates the one or more electrical components and includes an access window through which extends a second portion of the plurality of conductive leads. The access window is sized to receive a tab of a communications antenna.

Another general aspect includes a device, including: an enclosure for housing an electronics assembly. The enclosure includes a lid and a side wall connected to the lid. The device also includes a set of conductive pins extending through the lid of the enclosure. The device also includes a communications antenna connected to an exterior surface of the side wall, the communications antenna including a set of conductive terminals. The set of conductive pins is received by and electrically connected to the set of conductive terminals.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Figure 1:
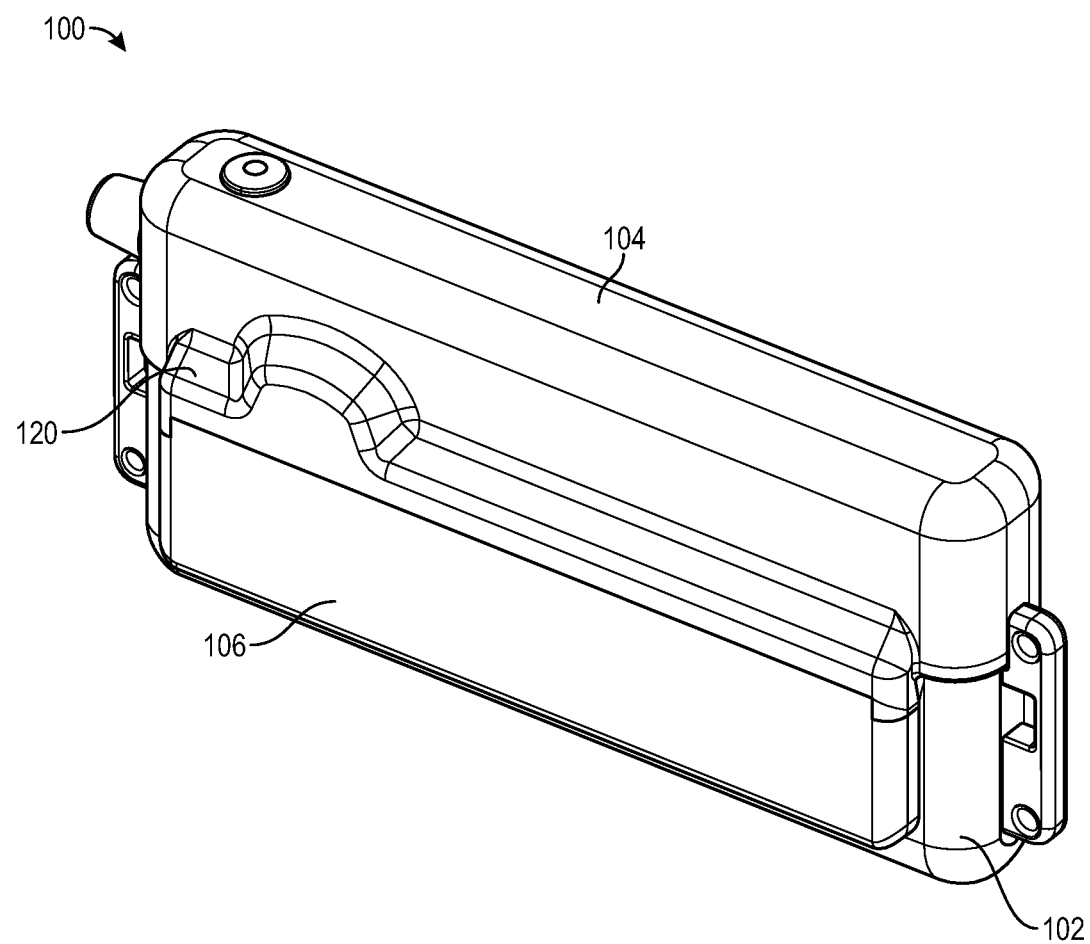
FIG. 1 illustrates a perspective view of an implantable medical device, according to at least one example.

Examples are described herein in the context of implantable medical devices such as implantable pulse generators ("IPGs") or other such devices for neuromodulation. Those of ordinary skill in the art will realize that the following description is illustrative only and is not intended to be in any way limiting. For example, the features described with respect to the implantable medical devices are applicable to any other medical device that is implanted into a person's body. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, an implantable medical device includes its active components (e.g., electronics and battery) either housed within a metal enclosure or encased in an epoxy header. The epoxy header includes an access window by which conductive leads from the active components are accessible. A communications antenna, which is formed in a ceramic substrate, is fully or partially encapsulated in epoxy as part of a separate process and connected to an exterior surface of the metal enclosure and apart from the header. A tab located at a top of the antenna includes conductive terminals which are mated with the conductive leads during assembly. The size and shape of the tab is formed to have a corresponding shape as the access window, but with slightly smaller dimensions to ensure that the tab fits within the access window. Once mated, the conductive leads are electrically connected with the conductive terminals using a laser welding process or other suitable process. A silicone or other bio-compatible material is then applied to fill in the access window. A bead of this material is also applied between a perimeter edge of the antenna that is adjacent the header and the header to create a smooth transition between the antenna and the header.

Conventional over-molding of header components may prove challenging because of the complicated fixture needed to hold all components in place during molding, the additional time required for epoxy to surround all components, and the additional time required for curing The described arrangement, however, reduces the amount of time needed for flowing epoxy around a complicated geometry on the top of the header and reduces the amount of cure time for the epoxy header as compared to headers that enclose communications antennas. Additionally, because of the simpler geometry on the top of enclosure, pre-molded headers may be practical, which may reduce production costs and production time. Because the communications antenna and the header are formed using different processes, a designer can select customized epoxies with different properties for the communications antenna as compared to the header (e.g., one for the header and a different one to encapsulate the antenna). Forming the communications antenna separate from the header also enables improved uniformity of the thickness of the epoxy. This ensures a more predictable operation of the communications antenna, which could be impacted by un-uniform surfaces. Forming the communications antenna separate from the header allows for a full cure cycle of the communication antenna because the antenna does not include any active components that could be harmed during the cure cycle. Finally, connecting the communications antenna to an exterior surface of the enclosure as described allows the antenna and the implantable medical device (without the antenna) to be manufactured in parallel, thereby obtaining the benefits of parallelization.

This illustrative example is given to introduce the reader to the general subject matter discussed herein and the disclosure is not limited to this example. The following sections describe various additional non-limiting examples of insect storage and dispensing systems.

Figure 2:
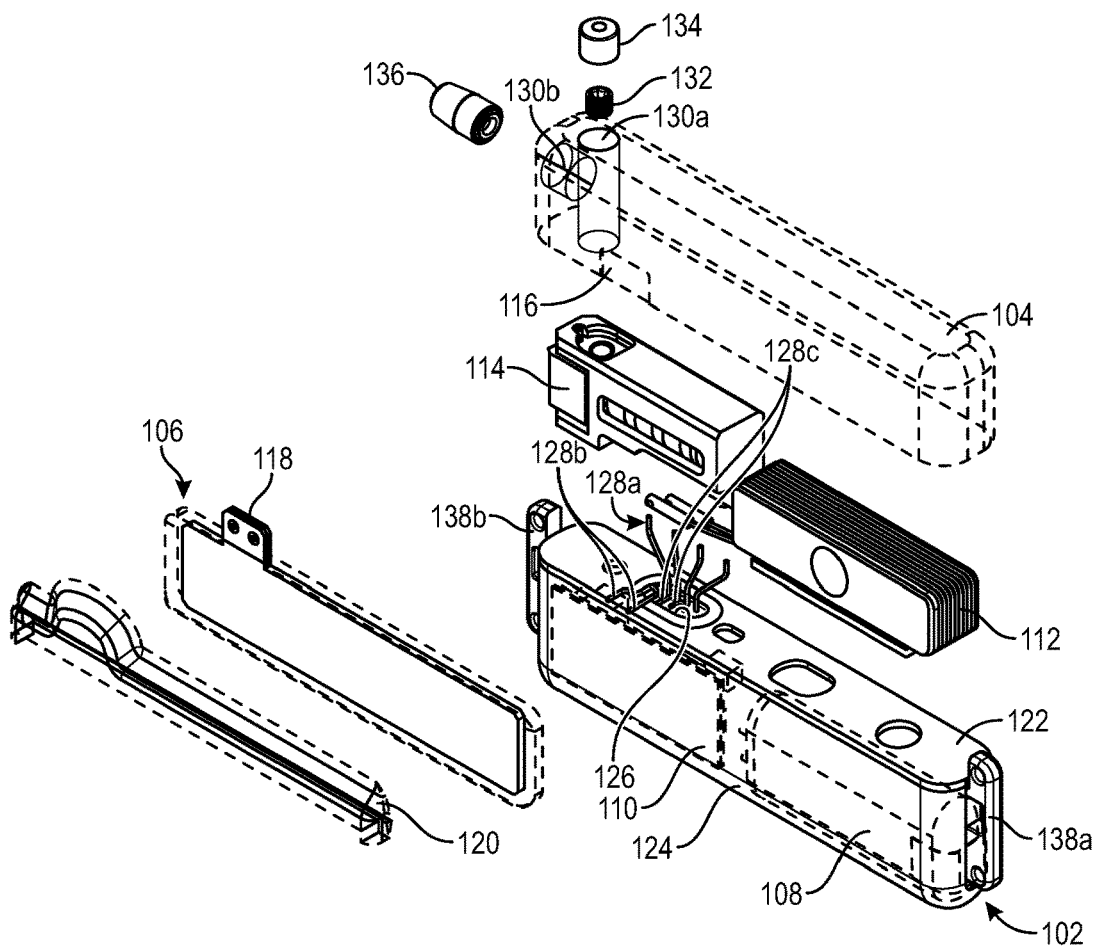
FIG. 2 illustrates an exploded view of the implantable medical device of FIG. 1, according to at least one example.

Referring now to the figures, FIG. 1 and FIG. 2 respectively illustrate a perspective view of an assembled example implantable medical device 100 and an exploded view of the example implantable medical device 100, according to at least one example. The illustrated implantable medical device 100 is an implantable pulse generator ("IPG") medical device for providing neuromodulation therapies. To provide such therapies, the implantable medical device 100 is inserted into a patient's tissue and connected to a neural interface (not shown). The neural interface is placed at a target location within the patient's body. The implantable medical device 100 then delivers electrical signals to the target location using the neural interface and records responses collected by the neural interface. Because the implantable medical device 100 will be inserted or otherwise implanted in the patient's skin, the implantable medical device 100 has a small form factor (e.g., about 40 mm long, about 20 mm tall, and about 7 mm wide in this example) and smooth edges to reduce the potential for patient irritation or injury during and after insertion. In some examples, the dimension of the implantable medical device 100 are greater than those listed or smaller than those listed.

Figure 4A:
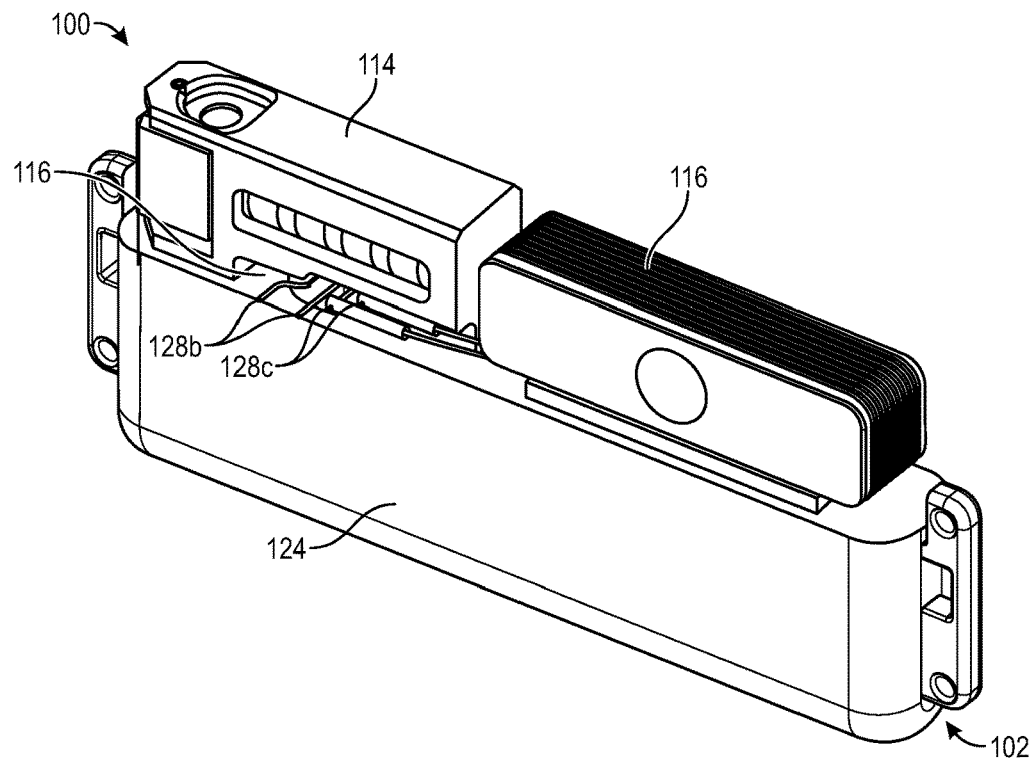
FIG. 4A illustrates a perspective view of a first state of formation of an implantable medical device, according to at least one example.

As illustrated in FIG. 1, generally, the implantable medical device 100 includes an enclosure 102 sometimes referred to as a canister, a header 104, and a communications antenna 106. The enclosure 102 is configured to house active components of the implantable medical device 100 such as one or more batteries 108 and an electronics assembly 110. The enclosure 102 is hermetically sealed thereby keeping the active components free from moisture exposure. The header 104 is configured to encase other active and/or passive components such as a charging antenna 112 and a connector stack 114 that are mounted to the enclosure 102. For example, as illustrated in FIG. 4A, the charging antenna 112 and the connector stack 114 are shown mounted to a lid of the enclosure 102.

Figure 4B:
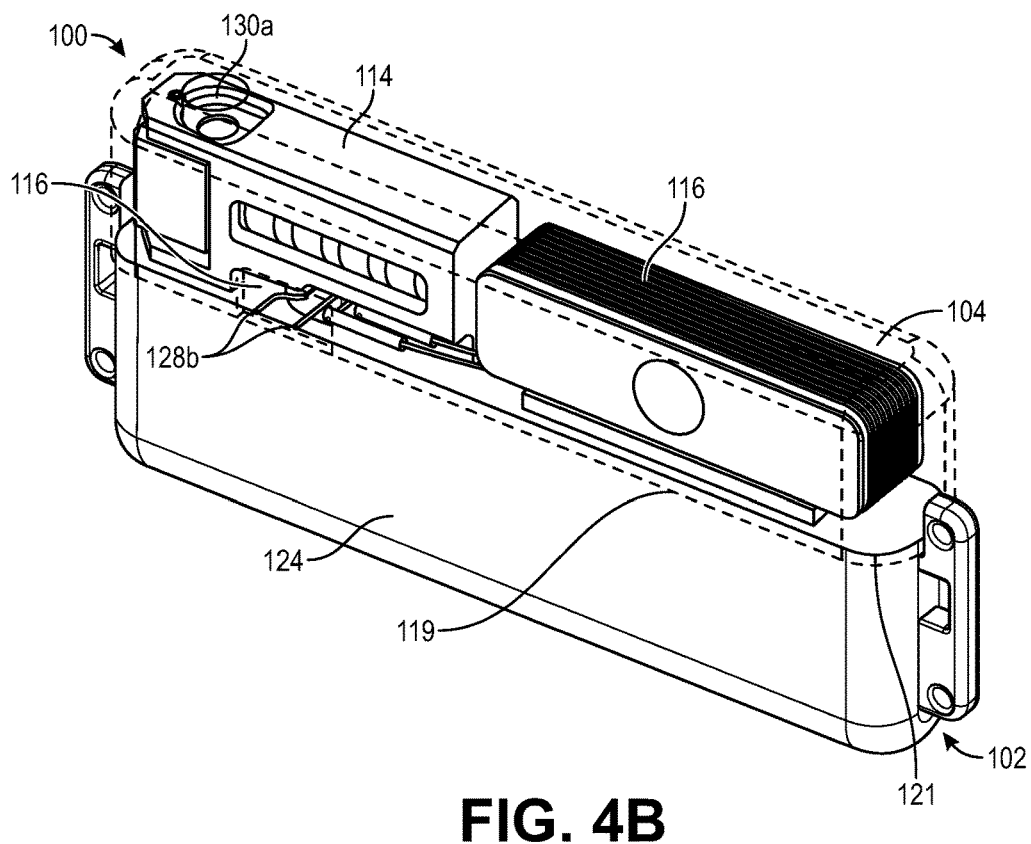
FIG. 4B illustrates a perspective view of a second state of formation of the implantable medical device of FIG. 4A, according to at least one example.

Connection points between the header 104 and the enclosure 102 are also hermetically sealed thereby preventing moisture ingress into the header space of the implantable medical device 100. For example, as illustrated in FIG. 4B, the header 104 can be formed from an epoxy that is over-molded and extends below a top surface of the enclosure 102 such that the header 104 surrounds the top surface of the enclosure 102 and at least a portion of the side walls of the enclosure 102. In FIG. 4B, a perimeter edge 119 of the header 104 extends below a perimeter edge 121 of the enclosure 102. As shown in more detail in FIG. 5, an access window 116 sometimes referred to as a weld window, which is sized and shaped to correspond to a tab 118 of the communications antenna 106, is also defined in the header 104. The access window 116 defines a cutaway region of the header 104 to provide access to components within the header 104.

Figure 4C:
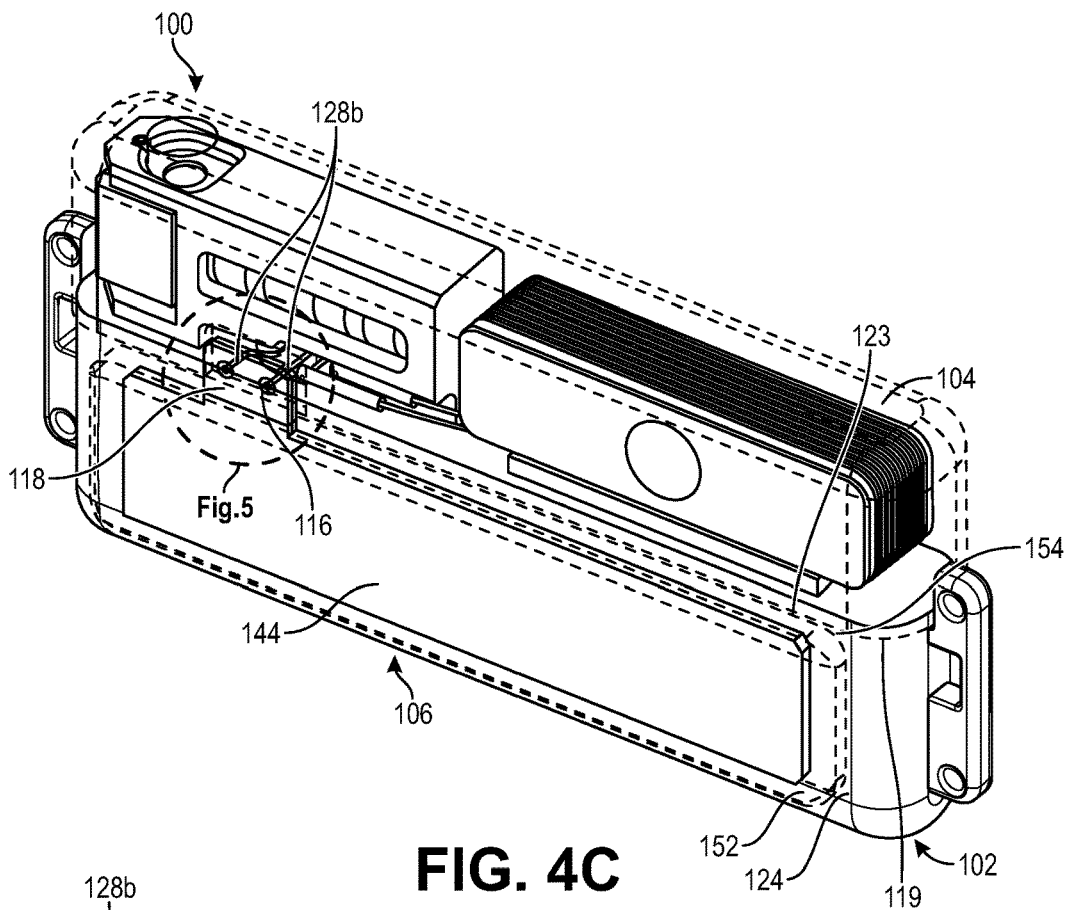
FIG. 4C illustrates a perspective view of a third state of formation of the implantable medical device of FIG. 4A, according to at least one example.
Figure 4D:
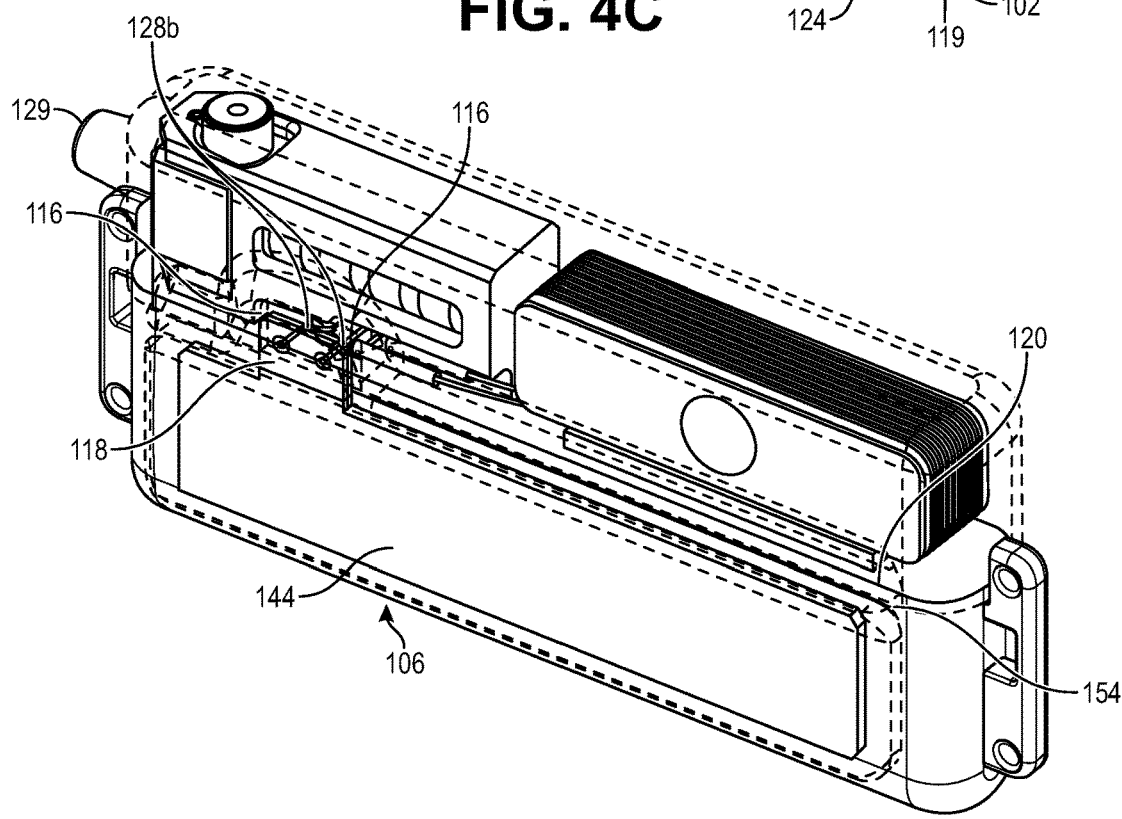
FIG. 4D illustrates a perspective view of a fourth state of formation of the implantable medical device of FIG. 4A, according to at least one example.

The communications antenna 106, which is formed as part of a separate process, is connected to the enclosure 102 such that the tab 118 fits within the access window 116, as illustrated in FIG. 4C. This enables electrical connections to be formed between components of the implantable medical device 100 with the communications antenna 106. As illustrated in FIG. 4D, once these connections have been made, a backfill 120 is applied to the access window 116 and, in some examples, to an air gap 154 between the communications antenna 106 and the header 104.

Turning now to the enclosure 102, the enclosure 102 includes a lid 122 and a container 124 having at least one side. The enclosure 102 is formed from a metallic material such as Titanium or other bio-compatible metallic material.

In some examples, some or a portion of the enclosure 102 is formed from a different rigid material which may or may not be metallic such as a bio-compatible epoxy. As used herein, the term bio-compatible material refers to a quality of not having toxic or injurious effects on biological systems (especially those of humans) and the capability of the material to exist in harmony with tissue without causing deleterious changes.

The container 124 and the lid 122 together define an interior volume of the enclosure 102. The battery 108 or other such power source and the electronics assembly 110 are mounted inside the interior volume, e.g., to an interior surface of the container 124. The container 124 may be formed from a single piece of material or from more than one piece of material. Depending on the shape of the container 124, the container 124 may include more than one side, e.g., a front side to which the communications antenna 106 is mounted, a back side opposite the front side, two lateral sides, and a bottom opposite the lid 122.

The electronics assembly 110 includes one or more electronic components configured for signal processing. For example, the electronics assembly 110 may include a system on chip ("SOC") or system in package ("SIP") that includes any suitable combination components for digital signal processing, analog signal processing, mixed-signal processing, and/or the like that may be present on the surface of a PCB assembly or embedded. Such components may include, for example, a microcontroller, a memory, a timing source, one or more digital interfaces, one or more analog interfaces, voltage regulators, and/or any other suitable component. The electronics assembly 110 may be configured to receive electrical signals from the neural interface, process such signals, and provide additional signals to the neural interface.

In some examples, the electronics assembly 110 includes a processing device and a computer-readable medium, such as a random access memory ("RAM") coupled to the processing device. The processing device may execute computer-executable program instructions stored in memory, such as executing one or more computer programs. Such processing devices may comprise a microprocessor, a digital signal processor ("DSP"), an application-specific integrated circuit ("ASIC"), field programmable gate arrays ("FPGAs"), state machines, or other processing means for processing electrical signals received from neural interface. Such processing means may further include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

The processing device may include, or may be in communication with, media, for example computer-readable storage media, that may store instructions that, when executed by the processing device, cause the processing device to perform steps as carried out, or assisted, by a processing device. Examples of computer-readable media may include, but are not limited to a memory chip, ROM, RAM, ASIC, or any other storage means from which a processing device can read or write information.

The container 124 includes smooth edges to minimize irritation during and after implantation. For example, as illustrated, the container 124 has an elongate, rectangular shape with a rounded bottom, i.e., the side opposite the lid 122. The vertical edges of the container 124 are also rounded. In some examples, the container 124 has a different shape than the one illustrated (e.g., round, ovate, square, etc.).

The container 124 includes one or more tabs 138. The tabs 138 may be used for manipulating the container 124 during manufacturing, implantation, or at other times. In some examples, the tabs 138 may be removable. For example, the tabs 138 may include frangible joints such that they can be removed prior to implantation. In some examples, the container 124 does not include the tabs 138.

Once the internal components have been mounted in the container 124, the lid 122 is sealed to the side(s) of the container 124. For example, a perimeter edge of an opening of the container 124 can be welded to a perimeter edge of the lid 122. In this example, the lid 122 is formed from a metallic material that is similar to the material of the container 124. The lid 122 may include a small hole, which may be used to backfill the internal volume of the container 124 with helium or other inert gas to provide an inert atmosphere within the internal volume. After which, the small hole may be welded shut. The container 124 and the lid 122, when connected, form a hermetic enclosure.

The lid 122 also includes a feedthrough 126. The feedthrough 126 is an opening that extends through the lid 122 and into the interior volume. The feedthrough 126 is used to pass through a set of feedthrough pins 128. The feedthrough pins 128 are conductive terminals that are connected to one or more of the power source 108, the electronics assembly 110, or other components within the container 124. In some examples, the feedthrough pins 128 carry electrical signals in the form of data and/or power. A first portion 128a of the feedthrough pins 128 are for electrically connecting the connector stack 114, for stimulation and sensing purposes through the neural interface. A second portion 128b of the feedthrough pins 128 are for electrically connecting the communications antenna 106. And a third portion 128c of the feedthrough pins are for electrically connecting the charging antenna 112. While a single feedthrough 126 is illustrated, in some examples, more than one feedthrough 126 is used, any of which may extend through the lid 122 and/or a side wall of the container 124. For example, the first portion 128a and the third portion 128c of the feedthrough pins 128 may extend through the lid 122 and the second portion 128b of the feedthrough pins 128 may extend through the front side wall of the container 124.

Turning now to the connector stack 114 and the charging antenna 112, the connector stack 114 is configured to receive a neural interface. For example, the connector stack 112 may include a port 129 to receive a plug of the neural interface. The connector stack 114 is fixedly mounted to the lid 122 and electrically connected to the first portion 128a of the feedthrough pins 128. The neural interface may include a plurality of conductive leads that are joined together in the plug. The plug, once inserted in to the port 129, connects individual conductive leads to the electronics assembly 110 via the feedthrough pins 128a. A long axis of the connector stack 114 is aligned with a long axis of the enclosure 102 in this example, though other alignments may be employed in some examples.

The charging antenna 112 is configured to receive an electromagnetic field (e.g., from an external charger) that is converted and used to charge the battery 108. The charging antenna 112 takes the form of a coil wrapped around a mandrel, however, the charging antenna 112 may take different form factors. In some examples, the charging antenna 112 receives signals at a different frequency than the communications antenna 106. The charging antenna 112 is fixedly mounted to the lid 122 and electrically connected to the third portion 128c of the feedthrough pins 128. A long axis of the charging antenna 112 is aligned with a long axis of the enclosure 102 in this example, though other alignments may be employed in some examples.

Turning now to the header 104, as illustrated in further detail in FIG. 4B, the header 104 is formed from a bio-compatible material such as an epoxy. The header 104 is either formed in place or pre-formed and mounted to the lid 122. The header 104 is configured to encapsulate the connector stack 114 and the charging antenna 112. As introduced previously, the header 104 includes the access window 116. The access window 116 is sized and shaped to correspond to the size and shape of the tab 118. Thus, the access window 116 functions as a block-out to enable access to the tab 118. As illustrated in FIG. 4B, the access window 116 also enables access to the second portion 128b of the feedthrough pins 128, e.g., the ones that bent about 90 degrees and extend toward an exterior side surface of the header 104.

The header 104 also includes one or more openings 130. The opening 130a is configured to receive a set screw 132 and a septum 134. The opening 130b is configured to receive a strain relief device 136. In some examples, the plug of the neural interface is inserted into the connector stack 114 via the opening 130b and the strain relief device 136.

Figure 3:
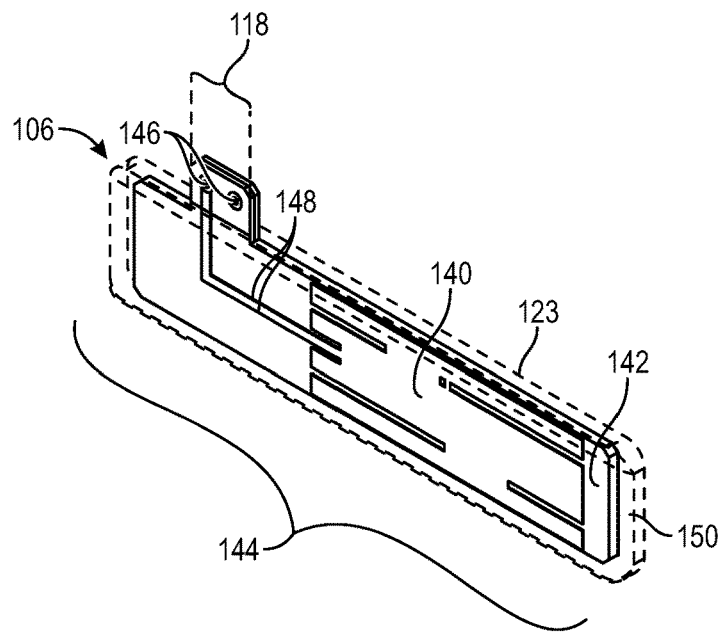
FIG. 3 illustrates a perspective view of a communications antenna, according to at least one example.

As illustrated in greater detail in FIG. 3, the communications antenna 106, which operates according to the Bluetooth® standard, includes a radiating surface 140 attached to a substrate 142 and a ground plane (not shown) located on the opposite, i.e., the side that faces the container 124. In some examples, the communications antenna 106 operates according to different standards or is configured differently. The communications antenna 106 functions to send and receive information relating to operation of the implantable medical device 100, e.g., measured parameters, configuration data, state data, control signals, any other information relating to the medical device 100, etc. The communications antenna 106 may enable pairing/communicating with a second device such as a programming unit, a charger, a mobile phone, or other device located outside the body. In some examples, the communications antenna 106 enables pairing/communicating with other devices located within the body.

The substrate 142, which is ceramic, includes the tab 118 and a main body 144. Thus the tab 118 and the main body 144 are formed from the same material and as part of the same substrate 142. The radiating surface 140 is attached to the substrate 142 in any suitable manner. For example, the radiating surface 140 can be deposited, printed, or otherwise attached to the substrate (e.g., pre-formed and glued). The shape of the radiating surface 140 is alterable depending on the radio-frequency characteristics desired. In some examples, the radiating surface 140 has a planar top surface and takes the form of a rectangular metallic plate. In other examples, the radiating surface 140 may take the form of other shapes. The two ferrules are used to connect to each of these circuits that are electrically isolated from each other on the antenna level (there is some coupling on the PCBA side).

The communications antenna 106 also includes a set of conductive terminals 146 located in the tab 118. A first conductive terminal 146 is electrically connected to the radiating surface 140 via a set of conductive traces 148. A second conductive terminal 146 is electrically connected to the ground plane via a second set of conductive traces (not shown). After the radiating surface 140, the conductive terminals 146, and the conductive traces 148 have been formed, the main body 144 is fully or partially encapsulated in a bio-compatible and radio frequency (RF)-compatible material such as epoxy or other suitable material, i.e., encapsulation 150. As used herein, the term RF-compatible material refers to a quality of the material that allows RF signals to pass through. In some examples, the RF-compatible material is an RF transparent material or one which RF fields can penetrate with no heat occurring.

In some examples, the entirety of the main body 144 (e.g., all surfaces) may be encapsulated in the encapsulation 150, all surfaces except for the backside surface opposite the container 124 may encapsulated (e.g., a bare backside encapsulation), all surfaces except for a portion of the backside surface opposite the container 124 may be encapsulated (e.g., a partially bare backside encapsulation), or any other suitable combination of surfaces or portions of surfaces may be encapsulated. The main body 144 is horizontally and vertically centered within the encapsulation 150. The depth of the encapsulation 150 on the front side of the communications antenna 106 may be about 0.8 mm and the depth on the back side may be about 0.3 mm. In some examples, the depths are greater than 0.8 mm or less than 0.3 mm. These depths may be selected to tune certain parameters of the communications antenna 106. For example, the operation of the radiating surface 140 may depend on the depth of the encapsulation 150 and/or properties of the epoxy used for the encapsulation 150. In some examples, the epoxy used for the encapsulation 150, the header 104, and other parts of the implantable medical device 100 is EPO-TEK brand MED-301 epoxy. In other examples, other epoxies having different properties are used such as those that are medical grade.

Figure 6:
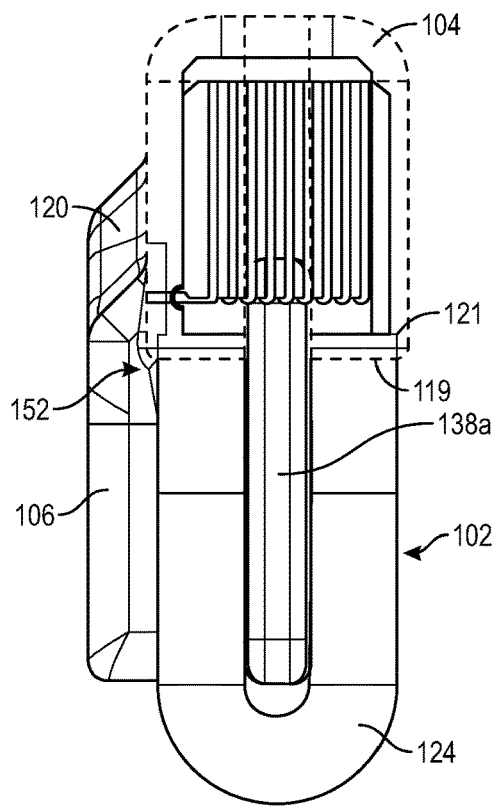
FIG. 6 illustrates an end view of the implantable medical device of FIG. 1, according to at least one example.

As illustrated in FIG. 4C, the communications antenna 106 is connected to an exterior surface of the container 124 (e.g., a mounting location) using any suitable adhesive. For example, additional epoxy, glue, or other adhesive may be applied to a backside of the communications antenna 106 and/or the exterior surface of the container 124 and the two parts may be joined together. The communications antenna 106 is positioned on the exterior surface of the container 124 in a manner that aligns the tab 118 with the access window 116 and forms a narrow air gap 154 between the perimeter edge 119 of the header 104 and a perimeter edge 123 of the communications antenna 106. The air gap 154 may provide volume for the backfill 120 to fill into during subsequent processing steps such as the one illustrated in FIG. 4D. As illustrated in FIG. 6, the air gap 154 is filled in when the backfill 120 is applied.

Figure 5:
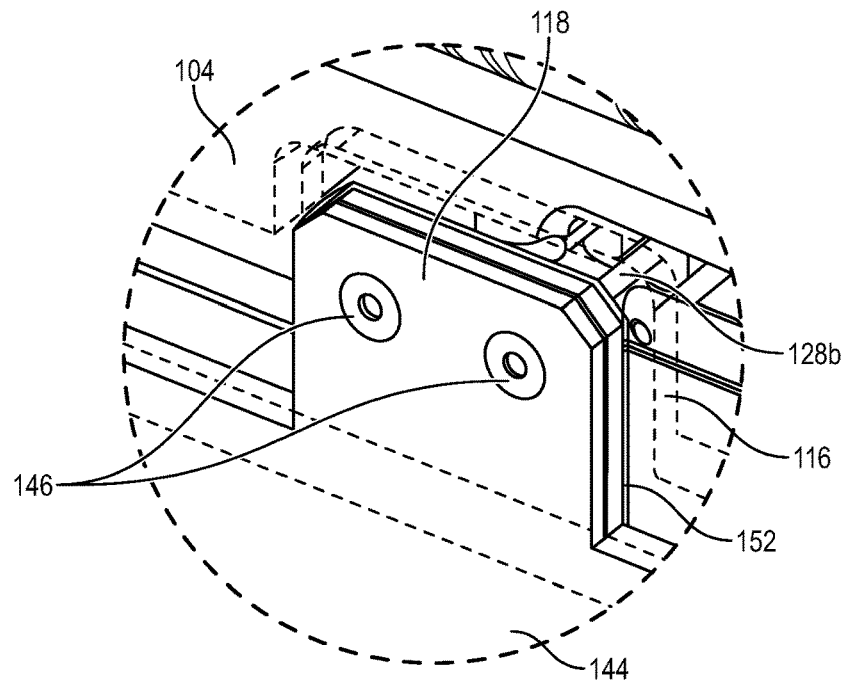
FIG. 5 illustrates a zoomed-in view of a portion of the implantable device illustrated in FIG. 4D, according to at least one example.

As illustrated in FIG. 5, after connecting the communications antenna 106 to the container 124 of the enclosure 102, the set of conductive terminals 146 are electrically connected to the second portion 128b of the set of feedthrough pins 128. In some examples, the set of conductive terminals 146 are plated vias sized and configured to receive the feedthrough pins 128. In some examples, the conductive terminals 146 include ferrules that receive the feedthrough pins 128. The electrical connections between the feedthrough pins 128 and the conductive terminals 146 are achieved using laser welding. In some examples, the electrical connections are formed using crimping, soldering, or any other suitable mechanical and/or energetic method.

Turning now to the backfill 120, the backfill 120, although illustrated in FIG. 2 as a rigid component, is a liquid bio-compatible material that, when applied to the implantable medical device 100 has roughly the shape shown in FIG. 2. The purpose of the backfill 120 is to seal up the volume of the access window 16 and, by doing, insulate the electrical connections formed in the tab 118 from outside moisture. Another purpose of the backfill 120 is to provide a smooth transition between the perimeter edge 119 of the header 104 and the perimeter edge 123 of the communications antenna 106. In this manner, the backfill 120 may create a filleted transition between the two parts. This distributes stresses across a broader area and makes for a smooth transition between the two parts. In some examples, the backfill 120 extends around additional portions of the perimeter edge of the communications antenna 106, e.g., vertical perimeter edges and horizontal perimeter edge. The backfill 120 can be formed from silicone, epoxy, a silicone epoxy mix, other flowable liquid adhesive, and/or any suitable combination of more than one material.

Figure 7:
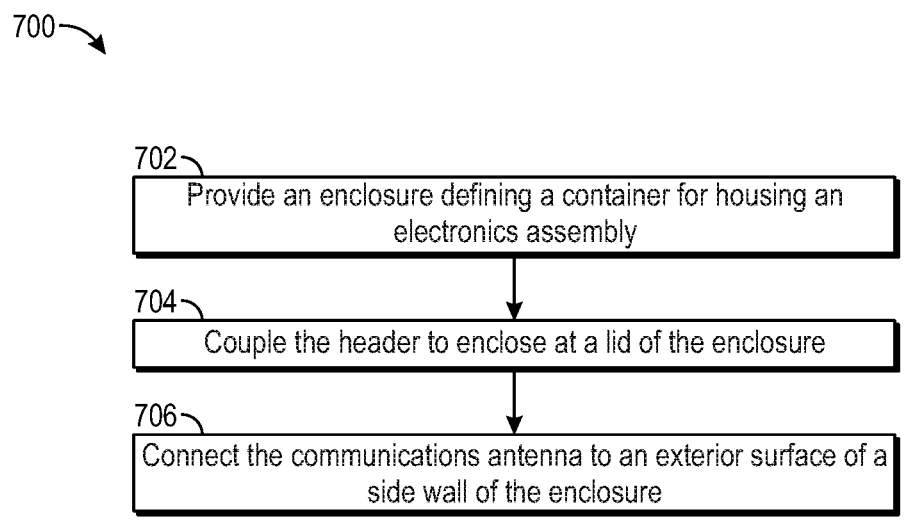
FIG. 7 illustrates a flow chart showing a process for forming an implantable medical device, according to at least one example.

FIG. 7 illustrates a flow chart showing a process 700 for forming an implantable medical device such as the implantable medical device 100, according to at least one example. The process 700 begins at block 702 by providing an enclosure 102 defining a container 124 for housing an electronics assembly 110. The process 700 may also include mounting at least one of a power source 108 and/or the electronics assembly 110 in the container 124.

At block 704, the process 700 includes coupling a header 104 to enclose at least a top portion of the enclosure 102. In some examples, this may include attaching a pre-manufactured header 104 in place or forming the header 104 in place. The header 102 includes an access window 116 located at the perimeter edge 119 of the header 102. At least some portion of set of conductive leads extend through the access window 116. For example, as illustrated in FIG. 4A, the feedthrough pins 128a, after coming through the feedthrough 126, include about a 90 degree bend to put distal ends of the feedthrough pins 128a in a position where they can be mated with the conductive terminals 146 of a tab 118 of a communications antenna 106.

At block 706, the process 700 includes connecting the communications antenna 106 to an exterior surface of a side wall of the enclosure 102. In this example, the communications antenna 106 includes a main body 144 and an electrical termination tab (e.g., the tab 118) that indexes in the access window 116 and aligns the set of conductive terminals 146 disposed in the electrical termination tab 118 with the set of conductive leads. In some examples, the electrical termination tab extends beyond the perimeter edge 121 of the enclosure 102 (e.g., beyond the lid 122) when the communications antenna 106 is connected to the enclosure 102.

In some examples, the main body 144 of the communications antenna 106 is encased in a bio-compatible material such as an encapsulation 150. In some examples, the header 104 is formed from a different bio-compatible material such as a different epoxy having different properties. Different epoxies may be selected to provide different radio-frequency (RF) properties, some for the communications antenna 106 and some for the charging antenna 112.

In some examples, the block 706 includes applying an adhesive to at least one of the communications antenna 106 or the side wall (e.g., a wall of the container 124), and mating together the communications antenna 106 and the side wall, with the adhesive disposed between the communications antenna 106 and the side wall.

In some examples, the process 700 further includes electrically connecting the set of conductive terminals 146 with the set of conductive leads. In some examples, this includes using laser welding.

In some examples, the process 700 further includes, after connecting the communications antenna 106 at the block 708, placing a backfill material 120 in the access window 116 to at least cover the set of conductive terminals 146. In this example, the block 708 includes placing the communications antenna 106 in a manner that an air gap 154 is formed between the perimeter edge 119 of the header 102 and a perimeter edge 123 of the communications antenna 106. In this example, the backfill material 120 is also placed in the air gap 154 to create a transition between the header 102 and the communications antenna 106.

In some examples, the process 700 further includes prior to performing the block 706, forming the communications antenna 106. This may include forming the main body 144 and the electrical termination tab 118 in a ceramic substrate 142, forming a metallic plate as the radiating surface 140 in the main body 144 of the ceramic substrate 142, forming the pair of conduct terminals 146 in the electrical termination tab 119, forming a pair of conductive traces 148 in the ceramic substrate 142 that electrically connect the metallic plate of the radiating surface 140 and at least one of pair of conductive terminals 146, and encasing the main body 144 in a bio-compatible material (e.g., the encapsulation 150) without encasing the electrical termination tab 118.

In some examples, the process 700 further includes forming a set of conductive leads (e.g., the feedthrough pins 128) that extend from the electronics assembly 110 and through the enclosure 102. In some examples, the set of conductive leads extend through a feedthrough 126 disposed in the lid 122 of the enclosure 102.

In the following, further examples are described to facilitate the understanding of the present disclosure.

Example 1. In this example, there is provided a device, including:
an enclosure including a lid and a side wall connected to the lid;
an electronics assembly disposed within an interior volume of the enclosure;
a set of conductive leads electrically connected to the electronics assembly and extending through the enclosure; and
a communications antenna disposed on an exterior surface of the side wall and including a main body and a tab, the tab including a set of conductive terminals, wherein the main body is coated in a bio-compatible material and the set of conductive terminals is electrically connected to the set of conductive leads.

Example 2. In this example, there is provided a device of any of the preceding or subsequent examples, further including:
a charging antenna connected to the lid; and
a connector stack connected to the lid,
wherein a second set of conductive leads extends through the enclosure and electrically connects the electronics assembly to at least one of the connector stack or the charging antenna.

Example 3. In this example, there is provided a device of any of the preceding or subsequent examples, further including an epoxy header that encloses the charging antenna and the connector stack.

Example 4. In this example, there is provided a device of any of the preceding or subsequent examples, wherein each conductive lead of the set of conductive leads extends through the lid of the enclosure in a first direction and includes a bend that orients a distal tip of the respective conductive lead in a second direction.

Example 5. In this example, there is provided a device of any of the preceding or subsequent examples, wherein the enclosure hermetically seals the interior volume.

Example 6. In this example, there is provided a device of any of the preceding or subsequent examples, wherein the bio-compatible material is RF-compatible.

Example 7. In this example, there is provided a device of any of the preceding or subsequent examples, wherein the communications antenna further includes a first metallic plate formed on a first side of a ceramic substrate and a second metallic plate formed on a second side of the ceramic substrate, and the set of conductive terminals is electrically connected to at least one of the first or second metallic plates via a set of conductive traces.

Example 8. In this example, there is provided a device of any of the preceding or subsequent examples, wherein the main body and the tab are formed from the ceramic substrate, with the metallic plate disposed in the main body.

Example 9. In this example, there is provided a method, including
  providing an enclosure including an electronics assembly;
  coupling a header to enclose at least a lid of the enclosure, wherein an access window is formed at a perimeter edge of the header, a set of conductive leads extending from the electronics assembly and through the access window; and
  connecting a communications antenna to an exterior surface of a side wall of the enclosure, the communications antenna including a body and an electrical termination tab that corresponds in size and shape to the access window and aligns a set of conductive terminals disposed in the electrical termination tab with the set of conductive leads.

Example 10. In this example, there is provided a method of any of the preceding or subsequent examples, further including electrically connecting the set of conductive terminals with the set of conductive leads.

Example 11. In this example, there is provided a method of any of the preceding or subsequent examples, wherein the body of the communications antenna is formed from a ceramic substrate that is coated in a bio-compatible material.

Example 12. In this example, there is provided a method of any of the preceding or subsequent examples, wherein the header is formed from a second bio-compatible material.

Example 13. In this example, there is provided a method of any of the preceding or subsequent examples, wherein the electrical termination tab extends beyond a perimeter edge of the lid of the enclosure.

Example 14. In this example, there is provided a method of any of the preceding or subsequent examples, wherein electrically connecting the set of conductive terminals with the set of conductive leads includes at least one of soldering, crimping, or laser welding.

Example 15. In this example, there is provided a method of any of the preceding or subsequent examples, wherein connecting the communications antenna to the exterior surface of the side wall includes:
  applying an adhesive to at least one of the communications antenna or the side wall; and
  mating together the communications antenna and the side wall, with the adhesive disposed between the communications antenna and the side wall.

Example 16. In this example, there is provided a method of any of the preceding or subsequent examples, further including forming the header.

Example 17. In this example, there is provided a method of any of the preceding or subsequent examples, wherein forming the header includes:
  forming the header as a separate part; and
  fitting the header in place on the lid of the enclosure after forming the header.

Example 18. In this example, there is provided a method of any of the preceding or subsequent examples, further including, after connecting the communications antenna, placing a backfill material in the access window to cover at least the set of conductive terminals.

Example 19. In this example, there is provided a method of any of the preceding or subsequent examples, wherein connecting the communications antenna to the exterior surface of the side wall includes connecting the communications antenna at a particular mounting location on the exterior surface that defines an air gap between the header and the communications antenna, and wherein placing the backfill material further includes placing the backfill material in the air gap.

Example 20. In this example, there is provided a method of any of the preceding or subsequent examples, further including, prior to connecting the communications antenna, forming the communications antenna by at least:
  forming the body and the electrical termination tab in a ceramic substrate;
  forming a metallic plate in the body of the ceramic substrate;
  forming the set of conduct terminals in the electrical termination tab;
  forming a pair of electrical traces in the ceramic substrate that electrically connecting the metallic plate and the set of conductive terminals; and
  encasing the body in a bio-compatible material without encasing the electrical termination tab.

Example 21. In this example, there is provided a system, including:
  an implantable medical device, including:
  an enclosure to house an electronics assembly, the enclosure including a lid and a side connected to the lid; and
  a set of conductive leads to extend from the electronics assembly to outside the enclosure via the lid; and
  an antenna that connects to an exterior surface of the side at a mounting location, the antenna including
    a body portion encased in a bio-compatible material;
    a tab portion connected to the body portion; and
    a set of conductive terminals disposed in the tab portion and that align with the set of conductive leads when the antenna is connected to the exterior surface at the mounting location.

Example 22. In this example, there is provided a system of any of the preceding or subsequent examples, wherein the antenna further includes a metallic plate disposed in the body portion and a set of conductive traces extending between the metallic plate and the set of conductive leads.

Example 23. In this example, there is provided a system of any of the preceding or subsequent examples, wherein a distal end of the tab portion extends beyond the lid of the enclosure when the antenna is connected to the exterior surface at the mounting location.

Example 24. In this example, there is provided a system of any of the preceding or subsequent examples, wherein the antenna includes an elongate shape.

Example 25. In this example, there is provided a system of any of the preceding or subsequent examples, wherein the implantable medical device further includes a header to encase at least the lid of the enclosure, wherein an access window is formed in the header that corresponds in shape to the tab portion.

Example 26. In this example, there is provided a system of any of the preceding or subsequent examples, wherein the bio-compatible material is epoxy and the header is formed from the epoxy.

Example 27. In this example, there is provided a system of any of the preceding or subsequent examples, further including a backfill to fill in the access window and to extend along at least a portion of the body portion adjacent the access window.

Example 28. In this example, there is provided a system of any of the preceding or subsequent examples, wherein the antenna operates in accordance with the Bluetooth® standard.

Example 29. In this example, there is provided a device, including:
- an enclosure including a lid and a side wall;
- an electronics assembly disposed within an interior volume of the enclosure and including a plurality of conductive leads that extend through the lid of the enclosure;
- one or more electrical components connected to an exterior surface of the lid and electrically connected to a first portion of the plurality of conductive leads; and
- a header that encapsulates the one or more electrical components and includes an access window through which extends a second portion of the plurality of conductive leads, the access window sized to receive a tab of a communications antenna.

Example 30. In this example, there is provided a device of any of the preceding or subsequent examples, further including the communications antenna, the communications antenna including the tab and a body.

Example 31. In this example, there is provided a device of any of the preceding or subsequent examples, wherein the body of the communications antenna is connected to an exterior surface of the side wall such that the tab aligns with the access window.

Example 32. In this example, there is provided a device of any of the preceding or subsequent examples, wherein the tab includes a set of conductive terminals that is electrically connected to the second portion of conductive leads.

Example 33. In this example, there is provided a device, including:
- an enclosure for housing an electronics assembly, the enclosure including a lid and a side wall connected to the lid;
- a set of conductive pins extending through the lid of the enclosure; and
- a communications antenna connected to an exterior surface of the side wall, the communications antenna including a set of conductive terminals, wherein the set of conductive pins is received by and electrically connected to the set of conductive terminals.

Example 34. In this example, there is provided a device of any of the preceding or subsequent examples, further including:
- one or more electrical components connected to the lid; and
- a header connected to the lid and encasing the lid and the one or more electrical components.

Example 35. In this example, there is provided a device of any of the preceding or subsequent examples, further wherein the header physically contacts the side wall.

Example 36. In this example, there is provided a device of any of the preceding or subsequent examples, further including a silicone backfill that physically contacts the header and at least a portion of the communications antenna.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An implantable device, comprising:
   an enclosure comprising a lid and a side wall connected to the lid;
   an electronics assembly disposed within an interior volume of the enclosure;
   a plurality of conductive leads electrically connected to the electronics assembly and extending through the enclosure;
   a header connected to the lid of the enclosure comprising an access window, wherein the plurality of conductive leads extends from the electronics assembly through the access window; and
   a communications antenna mounted on an exterior surface of the side wall and comprising a main body and a tab, the tab comprising a plurality of conductive terminals and corresponding in size and shape to the access window, wherein the main body is coated in a bio-compatible material and the plurality of conductive terminals is electrically connected to the plurality of conductive leads.

2. The implantable device of claim 1, wherein the main body of the communications antenna is not disposed within the header.

3. The implantable device of claim 1, further comprising:
   a charging antenna connected to the lid; and
   a connector stack connected to the lid,
   wherein a second plurality of conductive leads extends through the enclosure and electrically connects the electronics assembly to at least one of the connector stack or the charging antenna.

4. The implantable device of claim 3, further comprising an epoxy header that encloses the charging antenna and the connector stack.

5. The implantable device of claim 1, wherein each conductive lead of the plurality of conductive leads extends through the lid of the enclosure in a first direction and comprises a bend that orients a distal tip of the respective conductive lead in a second direction.

6. The implantable device of claim 1, wherein the enclosure hermetically seals the interior volume.

7. The implantable device of claim 1, wherein the bio-compatible material is RF-compatible.

8. The implantable device of claim 1, wherein the communications antenna further comprises a metallic plate formed on a ceramic substrate, and the plurality of conductive terminals is electrically connected to the metallic plate via a set of conductive traces.

9. The implantable device of claim 8, wherein the main body and the tab are formed from the ceramic substrate, with the metallic plate disposed in the main body.

10. A method, comprising:
    providing an enclosure comprising an electronics assembly;
    coupling a header to enclose at least a lid of the enclosure, wherein an access window is formed at a perimeter edge of the header, a plurality of conductive leads extending from the electronics assembly and through the access window; and
    connecting a communications antenna to an exterior surface of a side wall of the enclosure, the communications antenna comprising a body and an electrical termination tab that corresponds in size and shape to the access window and aligns a plurality of conductive terminals disposed in the electrical termination tab with the plurality of conductive leads.

11. The method of claim 10, further comprising electrically connecting the plurality of conductive terminals with the plurality of conductive leads.

12. The method of claim 11, wherein the body of the communications antenna is formed from a ceramic substrate that is coated in a bio-compatible material.

13. The method of claim 12, wherein the header is formed from a second bio-compatible material.

14. The method of claim 10, wherein the electrical termination tab extends beyond a perimeter edge of the lid of the enclosure.

15. The method of claim 10, wherein electrically connecting the plurality of conductive terminals with the plurality of conductive leads comprises at least one of soldering, crimping, or laser welding.

16. The method of claim 10, wherein connecting the communications antenna to the exterior surface of the side wall comprises:
    applying an adhesive to at least one of the communications antenna or the side wall; and
    mating together the communications antenna and the side wall, with the adhesive disposed between the communications antenna and the side wall.

17. The method of claim 10, further comprising forming the header.

18. The method of claim 17, wherein forming the header comprises:
    forming the header as a separate part; and
    fitting the header in place on the lid of the enclosure after forming the header.

19. The method of claim 10, further comprising, after connecting the communications antenna, placing a backfill material in the access window to cover at least the plurality of conductive terminals.

20. The method of claim 19, wherein connecting the communications antenna to the exterior surface of the side wall comprises connecting the communications antenna at a particular mounting location on the exterior surface that defines an air gap between the header and the communications antenna, and wherein placing the backfill material further comprises placing the backfill material in the air gap.

21. The method of claim 10, further comprising, prior to connecting the communications antenna, forming the communications antenna by at least:
    forming the body and the electrical termination tab in a ceramic substrate;
    forming a first metallic plate in a first side of the body of the ceramic substrate;
    forming a second metallic plate in a second side of the body of the ceramic substrate;
    forming the plurality of conductive terminals in the electrical termination tab;
    forming a set of electrical traces in the ceramic substrate that electrically connect the first and second metallic plates and the plurality of conductive terminals; and encasing the body in a bio-compatible material without encasing the electrical termination tab.

* * * * *